(12) United States Patent
Agarwal et al.

(10) Patent No.: US 6,287,316 B1
(45) Date of Patent: *Sep. 11, 2001

(54) KNITTED SURGICAL MESH

(75) Inventors: Vishvaroop Agarwal, Philadelphia; Robert Dougherty, Reading, both of PA (US)

(73) Assignee: Ethicon, Inc., Somerville, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/277,671

(22) Filed: Mar. 26, 1999

(51) Int. Cl.$^7$ .................................................. A61B 17/08
(52) U.S. Cl. .............................................. 606/151; 66/195
(58) Field of Search .............................. 66/195; 128/336, 128/334; 606/151

(56) References Cited

U.S. PATENT DOCUMENTS

| | | | |
|---|---|---|---|
| 4,015,451 | * | 4/1977 | Gajjar ...................................... 66/195 |
| 4,193,137 | | 3/1980 | Heck ........................................ 3/1.4 |
| 4,347,847 | * | 9/1982 | Usher ................................ 128/334 R |
| 4,452,245 | * | 6/1984 | Usher ................................ 128/334 R |
| 4,520,821 | | 6/1985 | Schmidt, et al. . |
| 4,633,873 | | 1/1987 | Dumican, et al. . |
| 4,652,264 | | 3/1987 | Dumican . |
| 4,655,221 | | 4/1987 | Devereux . |
| 4,769,038 | | 9/1988 | Bendavid, et al. . |
| 4,838,884 | | 6/1989 | Dumican, et al. .................... 604/364 |
| 5,002,551 | | 3/1991 | Linsky, et al. ........................ 606/151 |
| 5,292,328 | | 3/1994 | Hain, et al. ........................... 606/151 |
| 5,456,711 | | 10/1995 | Hudson . |

FOREIGN PATENT DOCUMENTS

| | | | |
|---|---|---|---|
| 0 159 502 A2 | 3/1985 | (EP) | ................................ A61F/2/02 |
| 0 537 769 A1 | 10/1992 | (EP) | ................................ A61L/31/00 |
| WO 98/14134 | 4/1998 | (WO) . | |
| WO 98/37813 | 9/1998 | (WO) | ............................ A61B/17/00 |

* cited by examiner

*Primary Examiner*—Michael Buiz
*Assistant Examiner*—Anthony S. King

(57) ABSTRACT

A knitted surgical mesh formed from a yarn. The knitted mesh has from 18 to 24 courses per inch and from 5 12 to 16 wales per inch, a flexibility of from 400–950 mg-cm/cm, a burst strength greater than 175 pounds per square inch, and a pore size percentage greater than 37%.

15 Claims, 2 Drawing Sheets

KNITTED SURGICAL MESH

FIELD OF THE INVENTION

This invention relates to a textile material and, in particular, to a surgical mesh of knit construction fabricated from a polypropylene monofilament yarn.

BACKGROUND

Hernia repairs are among the more common surgical operations which may employ a mesh fabric prosthesis. Such mesh fabric prostheses are also used in other surgical procedures including the repair of anatomical defects of the abdominal wall, diaphragm, and chest wall, correction of defects in the genitourinary system, and repair of traumatically damaged organs such as the spleen, liver or kidney.

Mesh fabrics for use in connection with hernia repairs are disclosed in U.S. Pat. Nos. 5,292,328, 4,769,038 and 2,671,444. Knitted and woven fabrics constructed from a variety of synthetic fibers and the use of the fabrics, in surgical repair are also discussed in U.S. Pat. Nos. 3,054,406; 3,124,136; 4,193,137; 4,347,847; 4,452,245; 4,520,821; 4,633,873; 4,652,264; 4,655,221; 4,838,884;. 5,002,551; and European Patent Application No. 334,046.

It is desirable for a surgical mesh fabric prosthesis to exhibit certain properties and characteristics. In particular, the mesh should have a burst strength sufficient to ensure that the mesh does not break or tear after insertion into a patient. The mesh should also have a pore size which allows tissue to penetrate or "grow through" the mesh, after the mesh has been inserted into a patient. In addition, the mesh should be constructed so as to provide memory (ability to resume it's shape after deformation), thereby facilitating the insertion of the mesh prosthesis into a patient during a surgical operation.

It is an object of the present invention to provide a knitted surgical mesh having a high burst strength and large pore size, which has a greater flexibility than known knitted surgical mesh fabrics.

These and other objects and advantages of the invention will become more fully apparent from the description and claims which follow or may be learned by the practice of the invention.

SUMMARY OF THE INVENTION

The present invention is directed to a knitted surgical mesh formed from a yarn. The knitted mesh has from 18 to 24 courses per inch and from 12 to 16 wales per inch, a flexibility of from 400 to 950 mg-cm, a burst strength greater than 175 pounds per square inch, and a pore size percentage greater than 37%.

BRIEF DESCRIPTION OF THE DRAWINGS

In order that the manner in which the above-recited and other advantages and objects of the invention are obtained and can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

DESCRIPTION OF THE PREFERRED EMBODIMENTS

Figure 1:
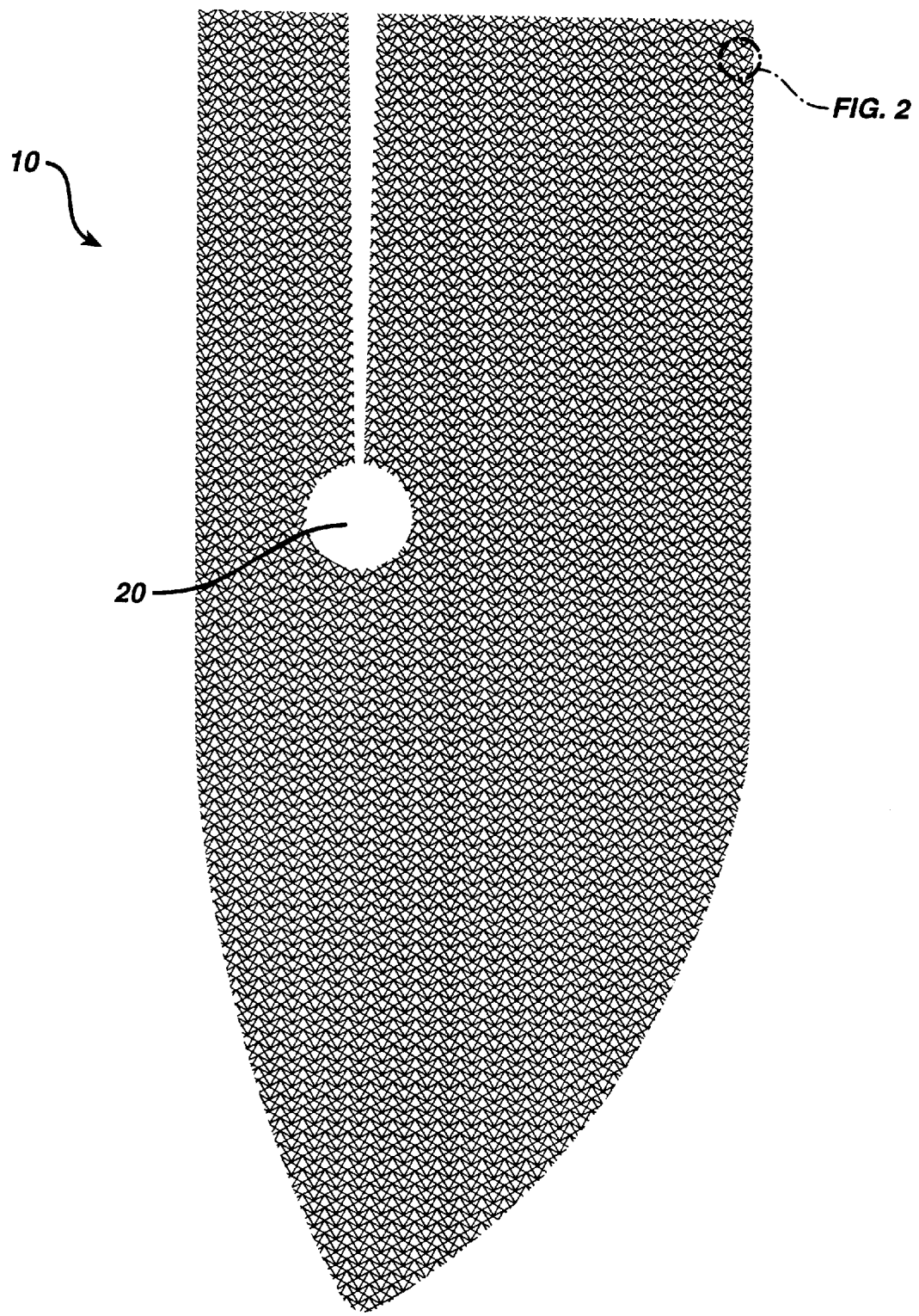
FIG. 1 is a diagram showing a knitted surgical mesh, in accordance with a preferred embodiment of the present invention.
Figure 2:
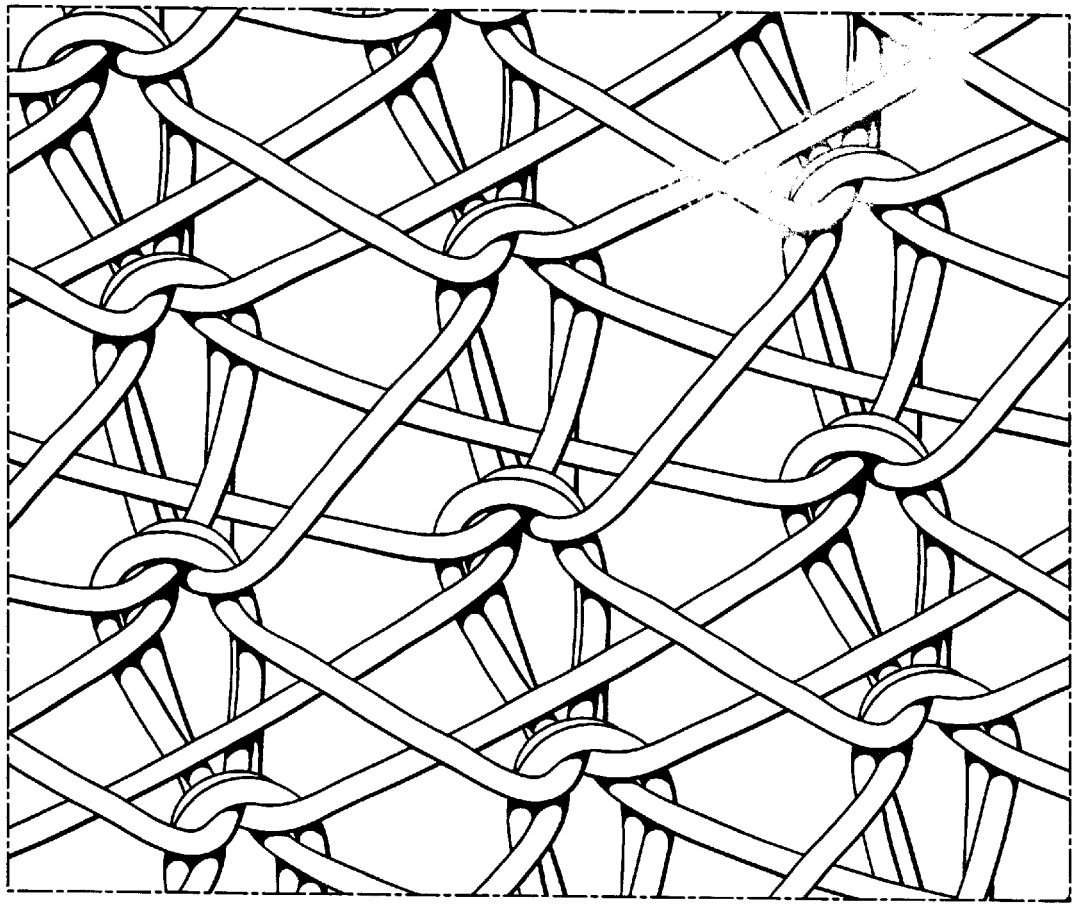
FIG. 2 is an enlarged view of a portion of the surgical mesh shown in FIG. 1.

The surgical mesh of this invention is preferably fabricated from a yarn that is biocompatible. Preferred are yarns that have already been accepted for use as a suture material. Numerous biocompatible absorbable and nonabsorbable yarns can be used to make the surgical meshes described hereinafter. Suitable nonabsorbable materials for use in the present invention include, but are not limited to, cotton, linen, silk, polyamides (polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride) polyolefins (e.g. polypropylene including isotactic and syndiotactic polypropylene and blends thereof, as well as, blends composed predominately of isotactic or syndiotactic polypropylene blended with heterotactic polypropylene (such as are described in U.S. Pat. No. 4,557,264 issued Dec. 10, 1985 assigned to Ethicon, Inc. hereby incorporated by reference) and polyethylene (such as is described in U.S. Pat. No. 4,557,264 issued Dec. 10, 1985 assigned to Ethicon, Inc. hereby incorporated by reference)) and combinations thereof. The preferred method for preparing the flexible polypropylene sutures of the present invention utilizes as the raw material pellets of isotactic polypropylene homopolymer having a weight average molecular weight of from about 260,00 to about 420,000. Polypropylene of the desired grade is commercially available in both powder and pellet form. Suitable absorbable materials for use as yarns include but are not limited to aliphatic polyesters which include but are not limited to homopolymers and copolymers of lactide (which includes lactic acid d-,l- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof. Fibers and/or yarns may be made from absorbable and nonabsorbable materials described above in heterologous yarns or bicomponent yarns. Additionally, fibers with different materials used in the sheath and core may also be used for the inventive surgical meshes.

In a preferred embodiment, the surgical mesh is fabricated from a monofilament yarn formed from a polypropylene resin, such as that disclosed in U.S. Pat. No. 4,911,165, entitled "Pliablized Polypropylene Surgical Filaments" and assigned to Ethicon, Inc., the contents of which is hereby incorporated in its entirety by reference. The preferred monofilament polypropylene yarn used has a denier of from about 30 to 300, and more preferably a denier of about 110. Alternatively, a multifilament yarn, such as a multifilament polypropylene yarn may be used to fabricate a surgical mesh in accordance with the present invention.

Lubricants are commonly applied to these yarns before the yarns are knitted. Suitable lubricants can be either nontoxic hydrophobic lubricants such as waxes (i.e. low-melting hydrocarbons or esters of fatty acids alcohols or blends thereof such as Ethasew™ wax) or hydrophilic lubricants such as polyalkyl glycols i.e. polyethylene glycol with a molecular weight of from about 200 to 10,000 (as described in WO 98/37813 hereby incorporated by reference). The preferred lubricant is Ethasew™ wax which is a mixture of 50 percent sorbitan monopalmitate, 20 percent sorbitan tri-stearate and 30 percent sorbitan tri-stearate containing 20 mole percent ethylene oxide.

The surgical mesh of this invention is preferably fabricated from a 110 denier monofilament polypropylene yarn by employing known and conventional warp knitting apparatus and techniques, such as the tricot and Raschel knitting machines and procedures described in "Warp Knitting Production" by Dr. S. Raz, Melliand Textilberichte GmbH, Rohrbacher Str. 76, D-6900 Heidelberg, Germany (1987), the contents of which are incorporated by reference herein. As is well known in the art of warp knitting, the number of courses and wales per inch in a knitted material is affected by a number of machine operating variables such as the rate at which the fabric is drawn away from the needles, the number of needles per inch, the amount of tension applied to the warp yarns and other variables after the fabric leaves the machine, e.g., the heat setting conditions. In the preferred embodiment of the present invention, the preferred polypropylene monofilament yarn described above is warp knitted, preferably tricot knitted on a 2 bar set-up, in accordance with the parameters set forth in Table I below:

TABLE I

| Courses per Inch | Wales per Inch | Back Bar | Front Bar |
| --- | --- | --- | --- |
| 18–24 | 12–16 | 1/0 | 1/2 |
|  |  | 2/3 | 1/0 |

Following knitting, the mesh is cleaned or scoured, and thereafter annealed to stabilize the fabric. For the latter operation, the mesh can be secured to a tenter frame which maintains the mesh at a predetermined width, the frame then being passed through an elongated heating zone at a temperature of from about 100° C. to about 160° C., preferably at a temperature of from about 120° C. to about 150° C., at a rate providing a dwell time of from about 0.5 to about 60 minutes and preferably from about 1.5 to about 25 minutes. Following heat setting, the mesh is cut to size, packaged and sterilized.

The mesh can be cut to any desired configuration, e.g., a square or rectangular shape of appropriate dimensions. A preferred configuration 10 having a key-hole opening 20 is shown in FIG. 1. An ultrasonic slitter may be employed to cut the mesh, various types of which are commercially available. Unlike the result one obtains when cutting with a blade, i.e., frayed yarn ends, or when the yarn ends are heat-sealed, i.e., bead-like formations, cutting the mesh to size with an ultrasonic cutter avoids both frayed and beaded ends.

The polypropylene monofilament knitted mesh fabricated as described above exhibits good memory. Depending on the yarn used to form the mesh, a mesh formed in accordance with Table I above preferably has a flexibility of about 400–950 mg-cm. In addition, depending on the yarn used to form the mesh, a mesh formed in accordance with Table I above preferably has a burst strength of about 175–250 pounds per square inch and, when the 110 denier monofilament yarn described above is used, the mesh has a mean burst strength of 240 pounds per square inch which varies between about 210 to 250 pounds per square inch depending on the sample. Finally, depending on the yarn used to form the mesh, a mesh formed in accordance with Table I above preferably has a pore size percentage of from about 37% to 50%, and, when the 110 denier monofilament yarn described above is used the mesh has a pore size of about 47%. The polypropylene monofilament knitted mesh fabricated as described above preferably possesses a thickness of from 18 to 25 mils depending on the particular yarn used, and when the 110 denier monofilament yarn described above is used, the mesh has a mean thickness of 20 mils which varies between about 18 to 21 mils depending on the sample. The pore size percentage is the percentage of the area in the plane of the mesh not blocked by the fibers of the knitted mesh. The flexibility, burst strength and pore size characteristics for a mesh fabric, fabricated as described above and other meshes that are currently commercially available, are compared in Table II set forth below:

TABLE II

| Mesh Fabric | Average Flexibility (mg-cm/cm) | Burst Strength (PSI) | Pore Size (%) | Thickness (Mils) |
| --- | --- | --- | --- | --- |
| Present Invention | 520 | 240 | 47.1 | 20.0 |
| MARLEX ™ Mesh (mfd. by C. R. Bard) | 786.3 | 186 | 41.3 | 25.9 |
| PROLENE ™ Mesh (mfd. by Ethicon, Inc.) | 678.0 | 257 | 49.73 | 24.1 |

As shown in Table II, the mesh of the present invention has: (i) a significantly better flexibility than the PROLENE™ and MARLEX™ surgical mesh fabrics, and (ii) a significantly higher burst strength and pore size percentage than the MARLEX™ mesh fabric.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. A knitted surgical mesh comprised of a knitted yarn, the knitted mesh having from 19 to about 24 courses per inch and from 12 to 16 wales per inch two bar warp knit construction with a bar pattern set-up of back bar 1/0, 2/3; front bar 1/2, 1/0, wherein the mesh has a burst strength from 210 to 250 pounds per square inch.

2. The surgical mesh of claim 1, wherein the yarn is a polypropylene yarn.

3. The surgical mesh of claim 2, wherein the yarn is a monofilament polypropylene yarn.

4. The surgical mesh of claim 3, wherein the yarn has a denier of from 30 to 300.

5. The knitted surgical mesh of claim 1, wherein the pore size percentage mesh is from about 35% to 60%.

6. The knitted surgical mesh of claim 5, wherein the pore size percentage of the mesh is from about 45% to about 50%.

7. The knitted surgical mesh of claim 1, wherein the mesh has a thickness of from 18 to 25 mils.

8. The knitted surgical mesh of claim 7, wherein the thickness of the mesh is from 18 to 21 mils.

9. The surgical mesh of claim 1, wherein the yarn is a multifilament yarn.

10. The surgical mesh of claim 9, wherein the yarn is made from polypropylene fiber.

11. The surgical mesh of claim 1, wherein the yarn is a monofilament yarn.

12. The surgical mesh of claim 11, wherein the yarn is made from polypropylene fiber.

13. The surgical mesh of claim 1, wherein the mesh includes a key-hole shaped opening within an interior region of the mesh.

14. The surgical mesh of claim 1, wherein the yarn is a nonabsorbable yarn made from a material selected from the group consisting of cotton, linen, silk, polyamides, polyesters, fluoropolymers, polyolefins and combinations thereof.

15. The surgical mesh of claim 1, wherein the yarn is an absorbable yarn made from a material selected from the group consisting of homopolymers and copolymers of lactide (which includes lactic acid d-, l- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

* * * * *

UNITED STATES PATENT AND TRADEMARK OFFICE
CERTIFICATE OF CORRECTION

PATENT NO. : 6,287,316 B1  Page 1 of 1
DATED : September 11, 2001
INVENTOR(S) : Vishvaroop Agarwal and Robert Dougherty It is certified that error appears in the above-identified patent and that said Letters Patent is hereby corrected as shown below:

<u>Column 4,</u>
Line 41, please delete "19" and insert therefore -- 18 --

Signed and Sealed this

Twentieth Day of April, 2004

JON W. DUDAS
*Acting Director of the United States Patent and Trademark Office*